(12) United States Patent
Kato et al.

(10) Patent No.: US 11,191,675 B2
(45) Date of Patent: Dec. 7, 2021

(54) METHOD FOR MANUFACTURING ABSORBENT BODY AND DEVICE FOR MANUFACTURING ABSORBENT BODY

(71) Applicant: KAO CORPORATION, Tokyo (JP)

(72) Inventors: Yuki Kato, Utsunomiya (JP); Tomoyuki Motegi, Ichikai-machi (JP)

(73) Assignee: KAO CORPORATION, Tokyo (JP)

( * ) Notice: Subject to any disclaimer, the term of this patent is extended or adjusted under 35 U.S.C. 154(b) by 30 days.

(21) Appl. No.: 16/650,607

(22) PCT Filed: Oct. 3, 2017

(86) PCT No.: PCT/JP2017/036034
§ 371 (c)(1),
(2) Date: Mar. 25, 2020

(87) PCT Pub. No.: WO2019/069383
PCT Pub. Date: Apr. 11, 2019

(65) Prior Publication Data
US 2021/0196527 A1 Jul. 1, 2021

(51) Int. Cl.
*A61F 13/15* (2006.01)
(52) U.S. Cl.
CPC .. *A61F 13/15723* (2013.01); *A61F 13/15642* (2013.01); *A61F 13/15658* (2013.01); *A61F 13/15764* (2013.01)
(58) Field of Classification Search
CPC .................................................... B29D 1/225
See application file for complete search history.

(56) References Cited

U.S. PATENT DOCUMENTS

| | | | |
|---|---|---|---|
| 6,573,422 | B1 | 6/2003 | Rosenfeld et al. |
| 2002/0147434 | A1 | 10/2002 | Mori |
| 2010/0174259 | A1 | 7/2010 | Mori |
| 2012/0312463 | A1 | 12/2012 | Ogasawara et al. |

(Continued)

FOREIGN PATENT DOCUMENTS

| | | |
|---|---|---|
| CN | 102573733 A | 7/2012 |
| CN | 105813609 A | 7/2016 |
| JP | 2002-301105 A | 10/2002 |

(Continued)

OTHER PUBLICATIONS

International Search Report issued in PCT/JP2017/036034 (PCT/ISA/210), dated Dec. 19, 2017.

*Primary Examiner* — Barbara J Musser
(74) *Attorney, Agent, or Firm* — Birch, Stewart, Kolasch & Birch, LLP (57) ABSTRACT

An absorbent member manufacturing method of the invention is a method for manufacturing an absorbent member (100) for an absorbent article and including synthetic fibers (10*b*). The method involves: a cutting step of cutting a continuous synthetic fiber sheet (10*bs*) at predetermined lengths in a first direction and a second direction intersecting with the first direction, and forming sheet fragments (10*bh*) including the synthetic fibers (10*b*); a transporting step of transporting the formed sheet fragments (10*bh*) to an accumulating portion (41); and an accumulating step of accumulating, in the accumulating portion (41), the sheet fragments (10*bh*) transported in the transporting step, and obtaining an accumulation (100*a*) which is a constituent member of the absorbent member (100).

17 Claims, 4 Drawing Sheets

(56) References Cited

U.S. PATENT DOCUMENTS

2013/0087289 A1    4/2013  Ogasawara et al.
2014/0308483 A1*  10/2014  Li .......................... A61F 13/536
                                                              428/167

FOREIGN PATENT DOCUMENTS

| | | |
|---|---|---|
| JP | 2005-126623 A | 5/2005 |
| JP | 2017-47212 A | 3/2017 |
| JP | 2017-70496 A | 4/2017 |
| JP | 2017-93776 A | 6/2017 |
| JP | 2019-63367 A | 4/2019 |
| JP | 2019-63368 A | 4/2019 |
| JP | 2019-63369 A | 4/2019 |
| JP | 2019-63370 A | 4/2019 |
| JP | 2019-63371 A | 4/2019 |
| JP | 2019-63372 A | 4/2019 |
| JP | 2019-63374 A | 4/2019 |
| JP | 2019-63375 A | 4/2019 |
| JP | 2019-97613 A | 6/2019 |
| JP | 2019-97614 A | 6/2019 |
| JP | 2019-170952 A | 10/2019 |
| RU | 2235559 C2 | 9/2004 |

* cited by examiner

METHOD FOR MANUFACTURING ABSORBENT BODY AND DEVICE FOR MANUFACTURING ABSORBENT BODY

TECHNICAL FIELD

The present invention relates to a method for manufacturing an absorbent member for an absorbent article, and a device for manufacturing an absorbent member.

BACKGROUND ART

A known example of an absorbent member used in an absorbent article, such as a disposable diaper, a sanitary napkin or an incontinence pad, is an absorbent member including pulp fibers and synthetic fibers. Patent Literature 1 is a known example describing a method for manufacturing an absorbent member including pulp fibers and synthetic fibers.

Patent Literature 1 describes a method for manufacturing an absorbent member for an absorbent article, the method involving: shaping a nonwoven fabric having a three-dimensional structure in which fibers have been bound together in advance; then forming nonwoven fabric fragments by pulverizing the nonwoven fabric; and mixing the nonwoven fabric fragments with hydrophilic fibers. Patent Literature 1 describes employing a cutter mill system as a means for pulverizing the nonwoven fabric.

CITATION LIST

Patent Literature

Patent Literature 1: JP 2002-301105A

SUMMARY OF INVENTION

The present invention is a method for manufacturing an absorbent member used for an absorbent article and including synthetic fibers. The manufacturing method involves: a cutting step of cutting a continuous synthetic fiber sheet including the synthetic fibers at predetermined lengths in a first direction and a second direction intersecting with the first direction, and forming sheet fragments including the synthetic fibers; a transporting step of transporting the formed sheet fragments to an accumulating portion; and an accumulating step of accumulating, in the accumulating portion, the sheet fragments transported in the transporting step, and obtaining an accumulation which is a constituent member of the absorbent member.

Further, the present invention is a device for manufacturing an absorbent member used for an absorbent article and including synthetic fibers. The manufacturing device includes: a duct that transports a material of the absorbent member; an accumulating portion that is arranged on a downstream side in a transporting direction within the duct and in which the material of the absorbent member is accumulated; and a supplying portion that supplies the synthetic fibers to inside the duct. The supplying portion includes cutter blades that cut a continuous synthetic fiber sheet including the synthetic fibers at predetermined lengths in a first direction and a second direction intersecting with the first direction, and form sheet fragments including the synthetic fibers.

DESCRIPTION OF EMBODIMENTS

When nonwoven fabric fragments are formed by pulverizing a nonwoven fabric by using a cutter mill system as in the absorbent member manufacturing method disclosed in Patent Literature 1, it is difficult to form nonwoven fabric fragments that all have a predetermined size, and there are variations with respect to the intended size. As a result, unevenness arises in the structure of the absorbent member including such nonwoven fabric fragments formed as above, which may cause an uncomfortable feeling of contacting a foreign object during use. Further, when unevenness arises in the structure of the absorbent member obtained as above, body fluid may not be absorbed stably when the absorbent member absorbs body fluid.

The present invention relates to providing an absorbent member manufacturing method capable of forming, with high precision, sheet fragments having an intended size, and capable of efficiently and continuously manufacturing absorbent members having an intended absorbency. The present invention also relates to providing an absorbent member manufacturing device capable of forming, with high precision, sheet fragments having an intended size, and capable of efficiently and continuously manufacturing absorbent members having an intended absorbency.

The present invention is described below according to preferred embodiments thereof with reference to the drawings.

Figure 1:
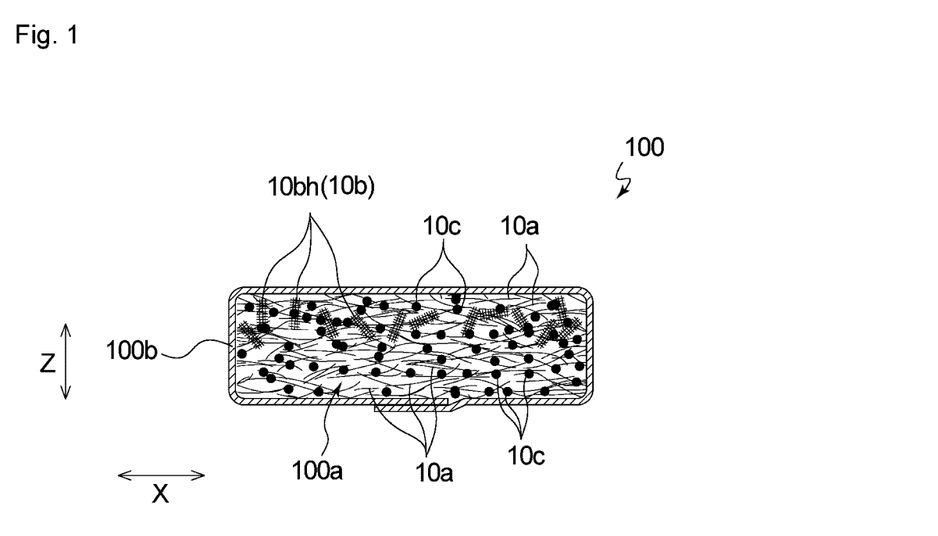
FIG. 1 is a cross-sectional view illustrating a preferred embodiment of an absorbent member manufactured by an absorbent member manufacturing method of the invention.

The manufacturing method of the invention is a method for manufacturing an absorbent member for an absorbent article. FIG. 1 illustrates a cross-sectional view of an embodiment of an absorbent member 100 manufactured by the absorbent member manufacturing method of the present embodiment. The absorbent member 100 includes synthetic fibers 10$b$, and as illustrated in FIG. 1, includes an accumulation 100$a$ including not only the synthetic fibers 10$b$ but also hydrophilic fibers 10$a$ and absorbent particles 10$c$. Herein, "include synthetic fibers 10$b$" refers to the inclusion of sheet fragments 10$bh$ including the synthetic fibers 10$b$. The absorbent member 100 may be a single layer or multi-layers including two or more layers so long as it includes the synthetic fibers 10$b$. In the present embodiment, the absorbent member 100 includes a two-layer structure accumulation 100$a$ in which an accumulation layer including the absorbent particles 10$c$ and fiber materials formed by mixing the hydrophilic fibers 10$a$ and the synthetic fibers 10$b$ is superposed on an accumulation layer including the absorbent particles 10$c$ and a fiber material made only of the hydrophilic fibers 10$a$. As described above, constituent members of the absorbent member 100 include the fiber materials and the absorbent particles 10$c$. The accumulation 100$a$ is a constituent member of the absorbent member 100, and the absorbent member 100 is formed by covering the two-layer structure accumulation 100$a$ with a core-wrap sheet 100$b$. The absorbent member 100 has a shape that is long in the longitudinal direction, which corresponds to the front-rear direction of a wearer when the absorbent article is worn.

The accumulation 100a includes a plurality of sheet fragments 10bh including the synthetic fibers 10b (simply referred to hereinafter also as "sheet fragments 10bh"). Each sheet fragment 10bh has a substantially rectangular shape. The average length of the sheet fragments 10bh is preferably from 0.3 to 30 mm, more preferably from 1 to 15 mm, even more preferably from 2 to 10 mm. Herein, in cases where each sheet fragment 10bh is a rectangle, the average length refers to the average value of the length of a side in the longitudinal direction. In cases where each sheet fragment 10bh is a square, the average length refers to the average value of the length of any one of the four sides. When the average length of the sheet fragments 10bh is 0.3 mm or greater, a sparse structure can easily be formed in the absorbent member 100. When the average length is 30 mm or less, the absorbent member 100 is less likely to cause an unnatural feel to the wearer, and absorbency is less likely to become uneven depending on the positions within the absorbent member 100. The average width of the sheet fragments 10bh is preferably from 0.1 to 10 mm, more preferably from 0.3 to 6 mm, even more preferably from 0.5 to 5 mm. Herein, in cases where each sheet fragment 10bh is a rectangle, the average width refers to the average value of the length of a side in the lateral direction. In cases where each sheet fragment 10bh is a square, the average width refers to the average value of the length of any one of the four sides. When the average width of the sheet fragments 10bh is 0.1 mm or greater, a sparse structure can easily be formed in the absorbent member 100. When the average width is 10 mm or less, the absorbent member 100 is less likely to cause an unnatural feel to the wearer, and absorbency is less likely to become uneven depending on the positions within the absorbent member 100.

The absorbent member manufactured according to the present invention can suitably be used as an absorbent member for an absorbent article. An absorbent article is used for absorbing and retaining body fluid excreted from the body, with examples mainly including urine and menstrual blood. Examples of absorbent articles include disposable diapers, sanitary napkins, incontinence pads, and pantiliners, but are not limited thereto, and widely encompass articles used for absorbing liquids discharged from the human body. Typically, an absorbent article includes a liquid-permeable topsheet, a liquid-impermeable or water-repellent backsheet, and a liquid-retentive absorbent member interposed between the two sheets. The absorbent member is the absorbent member formed by the absorbent member manufacturing method of the present invention. In cases of using the absorbent member manufactured by the present invention as an absorbent member of an absorbent article, for example, as illustrated in FIG. 1, the accumulation layer side including the absorbent particles 10c and the fiber materials formed by mixing the hydrophilic fibers 10a and the synthetic fibers 10b is arranged on the upper layer side which is on the skin side.

For the fiber materials forming the absorbent member 100, various materials conventionally used in absorbent members for absorbent articles can be used without particular limitation. Examples of the hydrophilic fibers 10a include pulp fibers, rayon fibers, and cotton fibers. Examples of the synthetic fibers 10b include short fibers made of polyethylene, polypropylene, or polyethylene terephthalate. The sheet fragments 10bh are not particularly limited so long as they are in a sheet form, but are preferably a nonwoven fabric. Further, constituent members constituting the absorbent member 100 not only include the hydrophilic fibers 10a and the synthetic fibers 10b, but also include absorbent particles 10c. Examples of the absorbent particles 10c include starch-based, cellulose-based, synthetic polymer-based, and superabsorbent polymer-based particles. Examples of superabsorbent polymers that may be used include starch-acrylic acid (acrylate) graft copolymers, saponified products of starch-acrylonitrile copolymers, crosslinked products of sodium carboxymethyl cellulose, and acrylic acid (acrylate) polymers. For constituent members constituting the absorbent member 100, it is also possible to use, for example, deodorants and antibacterial agents as necessary. Examples of the core-wrap sheet 100b include tissue paper and liquid-permeable nonwoven fabrics.

Figure 2:
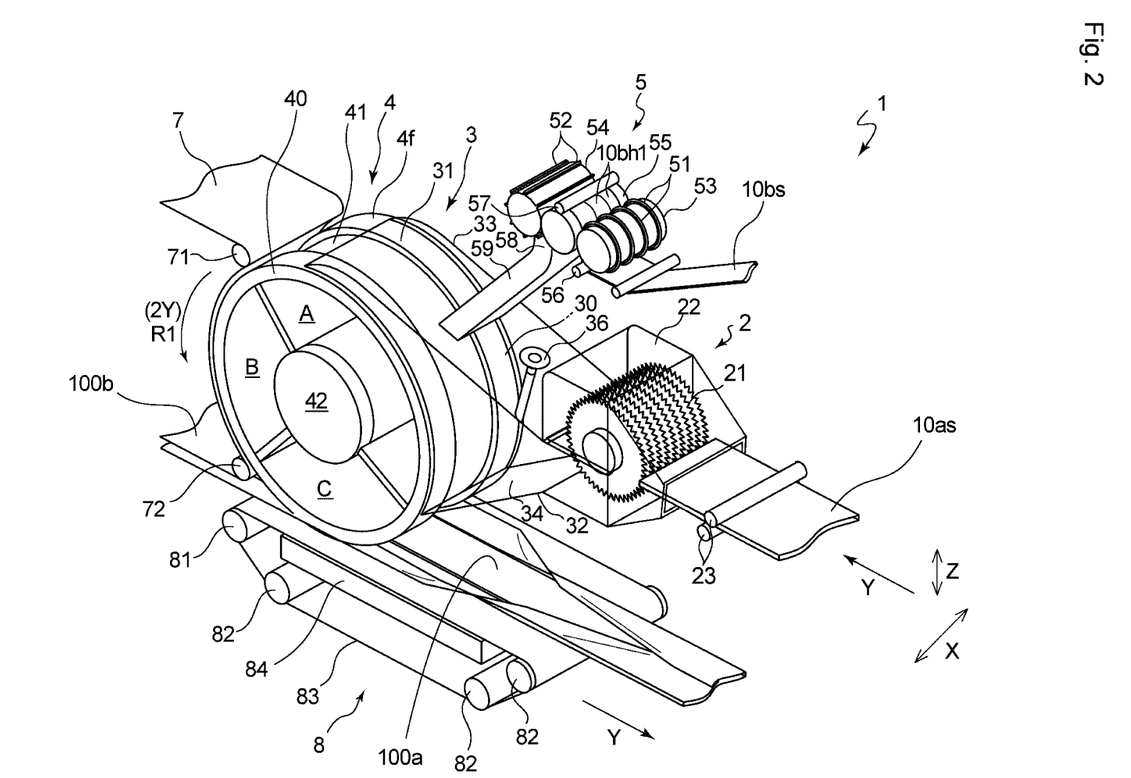
FIG. 2 is a schematic perspective view illustrating a preferred embodiment of a manufacturing device for manufacturing the absorbent member illustrated in FIG. 1.
Figure 3:
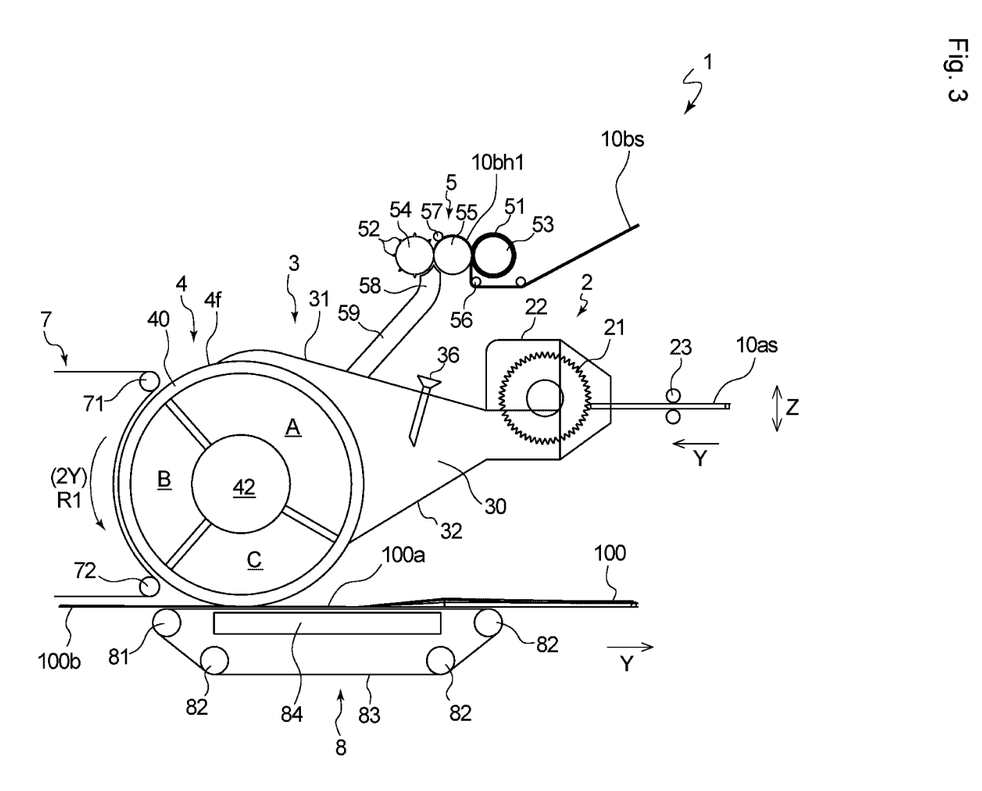
FIG. 3 is a schematic side view illustrating the manufacturing device illustrated in FIG. 2 as viewed from a lateral side.

Next, the absorbent member manufacturing method of the present invention is described with reference to FIGS. 2 to 4, taking, as an example, a method for manufacturing the absorbent member 100 according to the foregoing embodiment. FIGS. 2 and 3 illustrate an overall configuration of an embodiment of a manufacturing device 1 used for performing the manufacturing method of the present embodiment. On describing the method for manufacturing the absorbent member 100 of the present embodiment, first, the manufacturing device 1 will be described.

The material of the absorbent member only needs to include at least the synthetic fibers 10b, but the aforementioned absorbent member 100 includes the hydrophilic fibers 10a and the absorbent particles 10c in addition to the synthetic fibers 10b. As illustrated in FIGS. 2 and 3, the manufacturing device 1 for manufacturing the absorbent member 100 includes at least: a duct 3 that transports the material of the absorbent member 100; an accumulating depression 41, which is an example of an accumulating portion that is arranged on the downstream side in the transporting direction within the duct 3 and in which the material of the absorbent member 100 is accumulated; and a supplying portion 5 that supplies the synthetic fibers 10b to inside the duct 3. More specifically, the manufacturing device 1 includes, from the upstream side toward the downstream side in the transporting direction: a defibrating portion 2 that defibrates a hydrophilic sheet 10as including the hydrophilic fibers 10a by using a defibrating machine 21; a duct 3 that transports the material of the absorbent member 100 by carrying it on an airflow; a supplying portion 5 that supplies the synthetic fibers 10b to inside the duct 3 in midstream of the duct 3; a rotary drum 4 arranged downstream of the duct 3 adjacent thereto; a press-down belt 7 arranged along the rotary drum 4's outer circumferential surface 4f located on the opposite side from the duct 3; and a vacuum conveyor 8 arranged below the rotary drum 4. In the manufacturing device 1, the accumulating depression 41 is provided in the outer circumferential surface of the rotary drum 4.

In the description below, the direction in which the absorbent member 100 and a continuous synthetic fiber sheet 10bs including the synthetic fibers 10b are transported is described as the Y direction, the width direction of the synthetic fiber sheet 10bs and the absorbent member 100 being transported and the direction orthogonal to the transporting direction are described as the X direction, and the thickness direction of the synthetic fiber sheet 10bs and the absorbent member 100 being transported is described as the Z direction.

Further, the later-described first direction is the direction extending in the transporting direction Y, and refers to a direction wherein the angle formed between it and the transporting direction Y is within a range of less than 45 degrees. In the present embodiment, the first direction matches the direction parallel to the transporting direction Y.

Further, the later-described second direction is a direction intersecting with the first direction. In the present embodiment, the second direction is a direction orthogonal to the first direction, and matches the direction parallel to the width direction X of the synthetic fiber sheet 10*bs* and the absorbent member 100 being transported.

As illustrated in FIGS. 2 and 3, the manufacturing device 1 for manufacturing the absorbent member 100 including the hydrophilic fibers 10*a* includes a defibrating portion 2 that defibrates a continuous hydrophilic sheet 10*as* including the hydrophilic fibers 10*a*. The defibrating portion 2 includes: a defibrating machine 21 that defibrates the hydrophilic sheet 10*as*; and a casing 22 that covers the upper side of the defibrating machine 21. The defibrating portion 2 is a section that supplies, to inside the duct 3, the defibrated hydrophilic fibers 10*a* which is a material of the absorbent member 100. In the manufacturing device 1, the defibrating portion 2 also includes a pair of feed rollers 23, 23 that supplies the hydrophilic sheet 10*as* to the defibrating machine 21.

Of the pair of feed rollers 23, 23, at least one roller is structured so as to be rotated by a driving device (not illustrated). The feed rollers 23, 23 are nipping-type rollers. An example of the driving device is a servomotor. From the viewpoint of preventing slipping of the hydrophilic sheet 10*as*, it is preferable that both of the feed rollers 23, 23 are rotated by the driving device. In this case, the pair of feed rollers 23, 23 may be driven directly by the driving device, or one of the rollers may be driven by the driving device and the drive may be transmitted to the other roller by a transmission means such as a gear. From the viewpoint of further preventing slipping of the hydrophilic sheet 10*as*, the pair of feed rollers 23, 23 may be made less slippery by forming, in the surface thereof, grooves extending in the axial direction over the entire circumference. In addition to the pair of feed rollers 23, 23, other rollers for assisting the transportation of the hydrophilic sheet 10*as* may be provided.

As illustrated in FIGS. 2 and 3, the manufacturing device 1 includes a duct 3 that transports the material of the accumulation 100*a* of the absorbent member 100. The duct 3 extends from the defibrating portion 2 up to the rotary drum 4, and the duct 3's opening on the downstream side covers the outer circumferential surface 4*f* which is located at the rotary drum 4's space A which is maintained at a negative pressure. The duct 3 includes a top plate 31 forming the top surface, a bottom plate 32 forming the bottom surface, and side walls 33, 34 forming the respective side surfaces. By activating an air suction fan (not illustrated) of the rotary drum 4, an airflow for carrying the material of the absorbent member 100 toward the outer circumferential surface 4*f* of the rotary drum 4 is created inside the space surrounded by the top plate 31, the bottom plate 32, and the side walls 33, 34 of the duct 3. Stated differently, the inside of the duct 3 serves as a flow path 30.

Further, as illustrated in FIGS. 2 and 3, the manufacturing device 1 manufacturing the absorbent member 100 including the absorbent particles 10*c* has an absorbent particle dispersing tube 36 that supplies absorbent particles 10*c* into the duct 3, the absorbent particle dispersing tube being arranged at the top plate 31 of the duct 3. The absorbent particle dispersing tube 36 is configured such that the absorbent particles 10*c* are discharged, by a device such as a screw feeder (not illustrated), from a dispersing opening provided at the tip end of the absorbent particle dispersing tube 36, and are supplied into the duct 3. Further, the supply amount of the absorbent particles 10*c* to the absorbent particle dispersing tube 36 can be adjusted by the device such as a screw feeder. Thus, by adjusting the supply amount of the absorbent particles 10*c* to the absorbent particle dispersing tube 36 by a device such as a screw feeder, the amount of absorbent particles 10*c* dispersed to the flow path 30 can be adjusted freely, and as a result, the blending ratio of the absorbent particles 10*c* in the hydrophilic fibers 10*a* and the synthetic fibers 10*b* can be adjusted freely. In the manufacturing device 1, the absorbent particle dispersing tube 36 is arranged between the defibrating portion 2, which defibrates the hydrophilic sheet 10*as* into the hydrophilic fibers 10*a*, and the supplying portion 5 for the synthetic fibers 10*b*. By changing the arrangement position of the absorbent particle dispersing tube 36, the distribution of the absorbent particles 10*c* in the accumulation 100*a* of the absorbent member 100 can be adjusted. Further, by changing the height of the dispersing opening of the absorbent particle dispersing tube 36 (i.e., the distance between the top plate 31 and the dispersing opening of the absorbent particle dispersing tube 36), the distribution of the absorbent particles 10*c* in the thickness direction (Z direction) of the accumulation 100*a* of the absorbent member 100 can be adjusted.

As illustrated in FIGS. 2 and 3, the manufacturing device 1 includes a rotary drum 4. The rotary drum 4 has, in its outer circumferential surface 4*f*, an accumulating depression 41 which serves as an accumulating portion for accumulating the material of the absorbent member to obtain an accumulation. The rotary drum 4 is cylindrical, and, by receiving motive power from a prime mover (not illustrated) such as a motor, a member 40 forming the outer circumferential surface 4*f* rotates in the direction of arrow R1 about a horizontal axis. The rotary drum 4 includes: a member 40 forming the outer circumferential surface 4*f*; and a drum body 42 located more inward than the member 40. The drum body 42 is fixed and does not rotate. In the manufacturing device 1, the accumulating depression 41 of the rotary drum 4 is arranged continuously over the entire circumference in the circumferential direction (2Y direction) of the rotary drum 4. In the figure, 2Y indicates the circumferential direction of the rotary drum 4, and X indicates the width direction of the rotary drum 4 (i.e., direction parallel to the rotation axis of the rotary drum 4). As described above, the accumulating depression 41 in this manufacturing device 1 is arranged continuously over the entire circumference in the circumferential direction 2Y of the rotary drum 4, but may be configured so that a plurality of accumulating depressions are arranged at predetermined intervals in the circumferential direction 2Y of the rotary drum 4.

As illustrated in FIGS. 2 and 3, the drum body 42 of the rotary drum 4 has therein a plurality of spaces which are independent from one another, and in the manufacturing device 1, there are three spaces A to C, for example. The spaces A to C are partitioned off from one another by plates provided from the rotation axis side of the rotary drum 4 toward the outer circumferential surface 4*f* side. The rotary drum 4 is connected to an air suction fan (not illustrated) serving as an air suction mechanism. By driving the air suction fan, the pressure in the respective spaces partitioned off inside the rotary drum 4 can be adjusted. In the manufacturing device 1, the suction force in the region corresponding to the space A, which is the upstream region located in a region where the outer circumferential surface 4*f* is covered by the duct 3, can be made stronger or weaker than the suction force in the regions corresponding to the spaces B and C, which are downstream regions, and the space A is maintained at a negative pressure. Note, however, that the manner in which the spaces inside the drum body 42 are partitioned is not limited to the aforementioned configuration. For example, the drum body 42's space A which is maintained at a negative pressure may further be partitioned off into a plurality of spaces, and the pressure in each of the further-partitioned spaces may be adjusted. Further, for example, the drum body 42's space B may further be partitioned off into a plurality of spaces, and the pressure in each of the further-partitioned spaces may be adjusted; further, the pressure in the space located closest to the space A may be adjusted to match the pressure of the space A, so that a negative pressure region can be formed up to a point slightly ahead of where the accumulating depression 41 exits the duct 3.

As illustrated in FIGS. 2 and 3, the member 40 forming the outer circumferential surface 4f is arranged so as to cover the entire outer circumference of the drum body 42, and rotates in the direction of arrow R1 about a horizontal axis of the drum body 42 by receiving motive power from a prime mover such as a motor. The accumulating depression 41 is formed in the member 40 forming the outer circumferential surface 4f.

The bottom surface of the accumulating depression 41 is constituted by a porous member (not illustrated), and, while the accumulating depression 41 in the outer circumferential surface 4f passes over the space in the rotary drum 4 that is maintained at a negative pressure, the porous member functions as suction holes for sucking the material of the absorbent member 100.

As illustrated in FIGS. 2 and 3, the manufacturing device 1 includes a supplying portion 5 that supplies the sheet fragments 10bh to inside the duct 3. The supplying portion 5 includes cutter blades 51, 52 that cut a continuous synthetic fiber sheet 10bs including the synthetic fibers 10b at predetermined lengths in the first direction and the second direction, and form the sheet fragments 10bh including the synthetic fibers 10b. Preferably, the supplying portion 5 includes a suction nozzle 58 that sucks the sheet fragments 10bh formed by using the cutter blades 51, 52. In the manufacturing device 1, the supplying portion 5 includes a first cutter roller 53 including a plurality of cutter blades 51 that cut in the first direction, and a second cutter roller 54 including a plurality of cutter blades 52 that cut in the second direction. In the manufacturing device 1, the supplying portion 5 includes a single receiving roller 55 arranged in opposition to the first cutter roller 53 and the second cutter roller 54.

Figure 4:
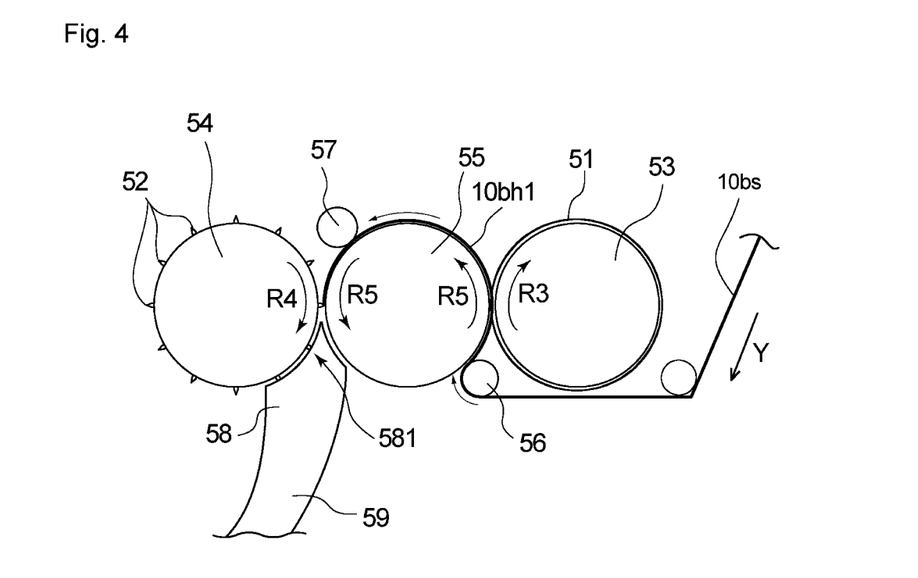
FIG. 4 is an enlarged side view illustrating a supplying portion of the manufacturing device illustrated in FIG. 2.

As illustrated in FIGS. 2 to 4, in the manufacturing device 1, the surface of the first cutter roller 53 is provided with a plurality of cutter blades 51, 51, 51, . . . extending continuously over the entire outer circumference of the first cutter roller 53 along the circumferential direction of the first cutter roller 53, the cutter blades being lined up in the axial direction (X direction) of the first cutter roller 53. By receiving motive power from a prime mover such as a motor, the first cutter roller 53 rotates in the direction of arrow R3. The interval between the cutter blades 51, 51, 51, . . . adjacent to one another in the axial direction of the first cutter roller 53 substantially corresponds to the width (length in the lateral direction; length in the X direction) of each sheet fragment 10bh formed by cutting and including the synthetic fibers 10b. Strictly speaking, depending on the tension during sheet transportation, the synthetic fiber sheet 10bs may be cut in a state where it is shrunken in the width direction X; thus, by releasing this tension, the width of each produced sheet fragment 10bh may become wider than the interval between the cutter blades 51, 51, 51, . . . .

In the manufacturing device 1, as illustrated in FIGS. 2 to 4, the surface of the second cutter roller 54 is provided with a plurality of cutter blades 52, 52, 52, . . . extending continuously over the entire width of the second cutter roller 54 along the axial direction (X direction) of the second cutter roller 54, the cutter blades being arranged with intervals therebetween in the circumferential direction of the second cutter roller 54. By receiving motive power from a prime mover such as a motor, the second cutter roller 54 rotates in the direction of arrow R4.

As illustrated in FIGS. 2 to 4, the receiving roller 55 is a flat roller having a flat surface. By receiving motive power from a prime mover such as a motor, the receiving roller 55 rotates in the direction of arrow R5. Opposing the surface of the receiving roller 55, the supplying portion 5 includes, in order from the upstream side toward the downstream side in the rotating direction (the direction of arrow R5): a free roller 56 that introduces the continuous synthetic fiber sheet 10bs between the receiving roller 55 and the first cutter roller 53; the first cutter roller 53 that cuts the continuous synthetic fiber sheet 10bs in the first direction (Y direction); a nip roller 57 that introduces, between the receiving roller 55 and the second cutter roller 54, a plurality of continuous sheet fragments 10bh1 that have been cut in the first direction and extend in the first direction (referred to hereinafter also as "continuous sheet fragment strips 10bh1"); and the second cutter roller 54 that cuts the continuous sheet fragment strips 10bh1 in the second direction (X direction). In the manufacturing device 1, the supplying portion 5 also includes a feed roller (not illustrated) that transports the continuous synthetic fiber sheet 10bs, and the feed roller introduces the continuous synthetic fiber sheet 10bs between the receiving roller 55 and the first cutter roller 53. The feed roller is configured so as to be rotated by a driving device such as a servomotor. From the viewpoint of preventing the synthetic fiber sheet 10bs from slipping, the feed roller may be made less slippery by forming, in the surface thereof, grooves extending in the axial direction over the entire circumference, or by subjecting the entire circumference to a coating treatment for increasing friction force. Further, slipping can be prevented by sandwiching the continuous synthetic fiber sheet 10bs between the feed roller and a nip roller.

As illustrated in FIGS. 2 to 4, the manufacturing device 1 includes a suction nozzle 58 that sucks the sheet fragments 10bh formed by the second cutter roller 54. The suction nozzle 58 has a suction opening 581 that is arranged below the second cutter roller 54—i.e., more toward the downstream side, in the second cutter roller 54's rotating direction (the direction of arrow R4), than the closest point between the second cutter roller 54 and the receiving roller 55. The suction opening 581 of the suction nozzle 58 extends over the entire width of the second cutter roller 54. From the viewpoint of improving the ability to suck the sheet fragments 10bh, the suction opening 581 of the suction nozzle 58 is arranged below the receiving roller 55 and the second cutter roller 54 so as to be in opposition between the receiving roller 55 and the second cutter roller 54. From the viewpoint of further improving the ability to suck the sheet fragments 10bh, the suction opening 581 of the suction nozzle 58 covers the outer surface of the second cutter roller 54 such that, as viewed from the side surface (i.e., in the axial direction) of the receiving roller 55 and the second cutter roller 54, the length of an arc of the suction opening 581 opposing the second cutter roller 54 is longer than the length of an arc of the suction opening 581 opposing the receiving roller 55, as illustrated in FIG. 4. More specifically, it is preferable that the suction opening 581 of the suction nozzle 58 covers the length of an arc that is at least one-fourth of the entire outer circumference of the second cutter roller 54, more preferably covers the length of an arc that is at least half of the entire outer circumference, as viewed from a side surface of the second cutter roller.

As illustrated in FIGS. 2 and 3, the suction nozzle 58 is connected by a suction tube 59 to the top plate 31 side of the duct 3. The sheet fragments 10*bh* sucked from the suction opening 581 of the suction nozzle 58 are supplied to inside the duct 3 in midstream of the duct 3 through the suction tube 59. In the manufacturing device 1, the connecting position of the suction tube 59 and the duct 3 is located between the defibrating portion 2 side and the rotary drum 4 side in the duct 3, and is located more toward the downstream side, in the duct 3, than the absorbent particle dispersing tube 36. The connecting position of the suction tube 59 and the duct 3 is, however, not limited thereto, and for example, it may be on the bottom plate 32 side and not the top plate 31 side of the duct 3.

In addition to the defibrating portion 2, the duct 3, the rotary drum 4, and the supplying portion 5 described above, the manufacturing device 1 also includes a press-down belt 7 and a vacuum conveyor 8.

As illustrated in FIGS. 2 and 3, the press-down belt 7 is arranged adjacent to the position of the duct 3 on the downstream side thereof along the rotary drum 4's outer circumferential surface 4*f*, and is arranged along the outer circumferential surface 4*f* located at the space B in which the pressure is set to zero (atmospheric pressure) or to a negative pressure weaker than that of the space A of the rotary drum 4. The press-down belt 7 is an endless, air-permeable or air-impermeable belt, bridges rollers 71 and 72, and rotates so as to follow the rotation of the rotary drum 4. In cases where the press-down belt 7 is an air-permeable belt, it is preferable that the belt substantially does not allow the material inside the accumulating depression 41 to pass therethrough. Thanks to the press-down belt 7, the accumulation 100*a* in the accumulating depression 41 can be retained inside the accumulating depression 41 until the accumulation is transferred onto the vacuum conveyor 8, even when the pressure in the space B is set to atmospheric pressure.

As illustrated in FIGS. 2 and 3, the vacuum conveyor 8 is arranged below the rotary drum 4, and is arranged at the outer circumferential surface 4*f* located in the rotary drum 4's space C in which the pressure is set to zero (atmospheric pressure) or to a slightly positive pressure. A weak positive pressure can be achieved by, for example, blowing air from the inside of the drum body 42 toward outside the outer circumferential surface 4*f*. The vacuum conveyor 8 includes: an endless air-permeable belt 83 that bridges a drive roller 81 and driven rollers 82, 82; and a vacuum box 84 arranged in a position opposing the outer circumferential surface 4*f* located at the space C of the rotary drum 4 across the air-permeable belt 83. A core-wrap sheet 100*b*, which is made of tissue paper or a liquid-permeable nonwoven fabric, is introduced onto the vacuum conveyor 8.

On the downstream side of the vacuum conveyor 8, the manufacturing device 1 further includes folding guide plates (not illustrated) which fold the core-wrap sheet 100*b* in the width direction (X direction) so as to cover the accumulation 100*a* transferred onto the core-wrap sheet 100*b*. In the manufacturing device 1, the folding guide plates fold, onto the accumulation 100*a*, both lateral sides of the core-wrap sheet 100*b* which extend along the transporting direction Y. Further, the manufacturing device 1 also includes a cutting device (not illustrated) on the downstream side of the folding guide plates. The cutting device manufactures separate absorbent members 100. For the cutting device, it is possible to use, without particular limitation, any type of device conventionally used for cutting a continuous strip of absorbent members in manufacturing absorbent articles, such as sanitary napkins, light incontinence pads, pantiliners, and diapers. An example of the cutting device is a pair of a cutter roller having a cutting blade on its circumferential surface and an anvil roller having a flat and smooth circumferential surface for receiving the cutting blade.

Next, a method for manufacturing an absorbent member 100 by using the aforementioned manufacturing device 1—i.e., an embodiment of the absorbent member manufacturing method of the present invention—will be described.

As illustrated in FIGS. 2 and 3, the method for manufacturing an absorbent member 100 involves: a cutting step of cutting a continuous synthetic fiber sheet 10*bs* including synthetic fibers 10*b* at predetermined lengths in the first direction and the second direction, and forming sheet fragments 10*bh* including the synthetic fibers 10*b*; a transporting step of transporting the formed sheet fragments 10*bh* to the accumulating depression 41 serving as an accumulating portion; and an accumulating step of accumulating, in the accumulating depression 41 serving as the accumulating portion, the sheet fragments 10*bh* transported in the transporting step, and obtaining an accumulation 100*a* which is a constituent member of the absorbent member. The method for manufacturing an absorbent member 100 according to the present embodiment involves a suction step of sucking the sheet fragments 10*bh* formed in the cutting step. In the transporting step, the sheet fragments 10*bh* sucked in the suction step are transported to the accumulating depression 41 by being carried on an airflow. Further, the method for manufacturing an absorbent member 100 according to the present embodiment involves a defibrating step of defibrating a continuous hydrophilic sheet 10*as* by using the defibrating machine 21 and obtaining hydrophilic fibers 10*a*. The method for manufacturing an absorbent member 100 according to the present embodiment will be described in detail below.

First, the space A inside the rotary drum 4 and the inside of the vacuum box 84 for the vacuum conveyor 8 are set to a negative pressure by activating air suction fans (not illustrated) respectively connected thereto. By creating a negative pressure inside the space A, an airflow for transporting the material of the absorbent member 100 to the outer circumferential surface 4*f* of the rotary drum 4 is created inside the duct 3. Further, the defibrating machine 21 and the rotary drum 4 are rotated, the first cutter roller 53, the second cutter roller 54 and the receiving roller 55 are rotated, and the press-down belt 7 and the vacuum conveyor 8 are activated.

Next, the defibrating step of defibrating a continuous hydrophilic sheet 10*as* by using the defibrating machine 21 and obtaining hydrophilic fibers 10*a* is performed. In the defibrating step, by using the feed rollers 23, the hydrophilic sheet 10*as* is supplied to the defibrating machine 21 and is defibrated thereby. The pair of feed rollers 23, 23 controls the speed for supplying the hydrophilic sheet 10*as* to the defibrating machine 21; in the defibrating step of the method for manufacturing an absorbent member 100 according to the present embodiment, the supplying of the hydrophilic sheet 10*as* to the defibrating machine 21 is controlled.

As illustrated in FIGS. 2 and 3, the hydrophilic sheet 10*as* supplied to the defibrating machine 21 is defibrated, and hydrophilic fibers 10*a*, which are a defibrated fiber material, are supplied from the defibrating machine 21 to the duct 3.

Further, in the method for manufacturing an absorbent member 100, the cutting step is performed, wherein the continuous synthetic fiber sheet 10*bs* is cut at predetermined lengths in the first direction (Y direction) and the second direction (X direction), to thereby form sheet fragments 10*bh* including synthetic fibers 10*b*. In the cutting step, as illustrated in FIG. 4, the continuous synthetic fiber sheet 10*bs* is cut at predetermined lengths in the first direction and the second direction and the sheet fragments 10*bh* are formed by using: the first cutter roller 53 including the cutter blades 51 that cut in the first direction; and the second cutter roller 54 including the cutter blades 52 that cut in the second direction. In the cutting step, by using the first cutter roller 53 which cuts the continuous synthetic fiber sheet 10*bs* at a predetermined length in the first direction, the second cutter roller 54 which cuts the sheet at a predetermined length in the second direction, and a single receiving roller 55 arranged in opposition to the first cutter roller 53 and the second cutter roller 54: the continuous synthetic fiber sheet 10*bs* is introduced between the first cutter roller 53 and the receiving roller 55 and is cut in the first direction to form continuous sheet fragment strips 10*bh*1; and the formed continuous sheet fragment strips 10*bh*1 are transported by the receiving roller 55 and are cut in the second direction between the second cutter roller 54 and the receiving roller 55 to form the sheet fragments 10*bh*. The cutting step is described in detail below.

In the cutting step, the synthetic fiber sheet 10*bs* is transported by using the aforementioned feed roller (not illustrated). The feed roller controls the speed for transporting the synthetic fiber sheet 10*bs*; in the cutting step of the method for manufacturing an absorbent member 100 according to the present embodiment, the transportation speed of the synthetic fiber sheet 10*bs* is controlled.

As illustrated in FIG. 4, in the cutting step, the synthetic fiber sheet 10*bs* transported by the feed roller is introduced, by the free roller 56, between the receiving roller 55 and the first cutter roller 53. The synthetic fiber sheet 10*bs* is introduced between the receiving roller 55, which is a flat roller rotating in the direction of arrow R5, and the first cutter roller 53, which rotates in the direction of arrow R3, and, with the plurality of cutter blades 51, 51, 51, . . . that are provided on the surface of the first cutter roller 53 and extend along the first direction (Y direction) with intervals therebetween in the second direction (X direction), the synthetic fiber sheet 10*bs* is cut in the first direction at positions with intervals therebetween in the second direction. Performing cutting as described above forms a plurality of continuous sheet fragment strips 10*bh*1 which extend in the first direction and are arranged side by side in the second direction. The plurality of cutter blades 51, 51, 51, . . . are arranged on the surface of the first cutter roller 53 at even intervals in the second direction. Thus, the synthetic fiber sheet 10*bs* is cut at even intervals, and a plurality of continuous sheet fragment strips 10*bh*1 having the same width (length in the second direction) are formed. From the viewpoint of ensuring that the sheet fragments 10*bh* have the necessary dimensions to achieve predetermined effects, it is preferable that the average width of the sheet fragment strips 10*bh*1 formed in the cutting step is from 0.1 to 10 mm, more preferably from 0.3 to 6 mm, even more preferably from 0.5 to 5 mm. In the present embodiment, the width of each sheet fragment strip 10*bh*1 cut by the first cutter roller 53 matches the length of the side, in the lateral direction, of each sheet fragment 10*bh* ultimately formed. Cutting, however, may be performed such that the width of each sheet fragment strip 10*bh*1 cut by the first cutter roller 53 corresponds to the length of the side, in the length direction, of each sheet fragment 10*bh* ultimately formed. In this case, the average width of the sheet fragment strips 10*bh*1 cut by the first cutter roller 53 is preferably from 0.3 to 30 mm, more preferably from 1 to 15 mm, even more preferably from 2 to 10 mm. The plurality of continuous sheet fragment strips 10*bh*1 that have been formed are transported on the circumferential surface of the receiving roller 55 which rotates in the direction of arrow R5, are transported between the receiving roller 55 and the nip roller 57, and are introduced between the receiving roller 55 and the second cutter roller 54 by the nip roller 57.

Next, as illustrated in FIG. 4, in the cutting step, the plurality of continuous sheet fragment strips 10*bh*1, which are arranged side by side in the second direction and extend in the first direction, are introduced between the receiving roller 55, which rotates in the direction of arrow R5, and the second cutter roller 54, which rotates in the direction of arrow R4, and, with the plurality of cutter blades 52, 52, 52, . . . that are provided on the surface of the second cutter roller 54 and extend over the entire width of the roller along the second direction with even intervals therebetween in the rotating direction of the second cutter roller 54, the plurality of continuous sheet fragment strips 10*bh*1 are cut along the second direction and intermittently in the first direction. Performing cutting as described above forms a plurality of rectangular sheet fragments 10*bh* in which the length in the first direction is longer than the length in the second direction. The plurality of cutter blades 52, 52, 52, . . . are arranged on the surface of the second cutter roller 54 at even intervals in the circumferential direction thereof. Thus, the plurality of sheet fragment strips 10*bh*1 are cut at even intervals, and a plurality of rectangular sheet fragments 10*bh* having the same length in the first direction are formed. From the viewpoint of ensuring that the sheet fragments 10*bh* have the necessary dimensions to achieve predetermined effects, it is preferable that the average length of each sheet fragment 10*bh* formed in the cutting step is from 0.3 to 30 mm, more preferably from 1 to 15 mm, even more preferably from 2 to 10 mm. In the present embodiment, the length of each sheet fragment 10*bh* cut by the second cutter roller 54 matches the length of the side, in the length direction, of each sheet fragment 10*bh*. Cutting, however, may be performed such that the length of each sheet fragment 10*bh* cut by the second cutter roller 54 corresponds to the length of the side, in the lateral direction, of each sheet fragment 10*bh*. In this case, the length (width) of each sheet fragment 10*bh* cut by the second cutter roller 54 is preferably from 0.1 to 10 mm, more preferably from 0.3 to 6 mm, even more preferably from 0.5 to 5 mm.

In the cutting step, the continuous synthetic fiber sheet 10*bs* is cut at predetermined lengths in the first direction and the second direction to thereby obtain the sheet fragments 10*bh* including the synthetic fibers 10*b*. Thus, the size of the obtained sheet fragments 10*bh* can easily be adjusted to an intended size, and a large amount of sheet fragments 10*bh* with the same size can easily be manufactured with high precision. As described above, since the sheet fragments 10*bh* with an intended size can be formed with high precision, it is possible to efficiently and continuously manufacture absorbent members having an intended absorbency.

Next, a suction step is performed for sucking the sheet fragments 10*bh* formed in the cutting step. In the manufacturing device 1, the supplying portion 5 includes the suction nozzle 58 whose suction opening 581 is arranged below the second cutter roller 54—i.e., more toward the downstream side, in the second cutter roller 54's rotating direction (the direction of arrow R4), than the closest point between the second cutter roller 54 and the receiving roller 55—as illustrated in FIGS. 2 and 3. In the suction step, the sheet fragments 10*bh* cut and formed by cutter rollers 53, 54 are sucked by using the suction nozzle 58. By arranging the suction opening 581 of the suction nozzle 58 below the second cutter roller 54—i.e., more toward the downstream side, in the second cutter roller 54's rotating direction R4, than the closest point between the second cutter roller 54 and the receiving roller 55—the plurality of sheet fragments 10*bh* cut and formed by the second cutter roller 54 and the receiving roller 55 can be sucked efficiently. Generally speaking, in cases where cutting is performed by the second cutter roller 54 and the receiving roller 55, the plurality of sheet fragments 10*bh* that have been cut and formed are likely to remain on the circumferential surface of the second cutter roller 54. In the manufacturing device 1, however, since the suction opening 581 of the suction nozzle 58 covers the length of an arc that is at least one-fourth of the entire outer circumference of the second cutter roller 54 as viewed from the side surface thereof, the plurality of sheet fragments 10*bh* remaining on the circumferential surface of the second cutter roller 54 can be sucked more efficiently.

Next, a transporting step is performed for transporting the formed sheet fragments 10*bh* to the accumulating depression 41 which is the accumulating portion. In the transporting step, the sheet fragments 10*bh* sucked in the suction step are transported to the accumulating depression 41 in the outer circumferential surface 4*f* of the rotary drum 4 by being carried on an airflow. The sheet fragments 10*bh* sucked in the suction step are supplied to inside the duct 3 through the suction tube 59. In the transporting step using the supplying portion 5, the plurality of sheet fragments 10*bh*, having undergone the cutting step and the suction step, are supplied to inside the duct 3 from the top plate 31 side of the duct 3 at a position in midstream of the transporting direction Y of the duct 3, and the supplied sheet fragments 10*bh* are transported in a dispersed and airborne state to the accumulating depression 41 of the rotary drum 4 by being carried on an airflow.

In the transporting step, the sheet fragments 10*bh* are mixed with the hydrophilic fibers 10*a* while the sheet fragments 10*bh* formed in the cutting step and the hydrophilic fibers 10*a* obtained in the defibrating step are being transported to the accumulating depression 41. In the transporting step, the hydrophilic fibers 10*a* formed in the defibrating step are supplied to inside the duct 3, and the plurality of sheet fragments 10*bh* having undergone the suction step are supplied to inside the duct 3 in midstream of the duct 3. Thus, the sheet fragments 10*bh* are transported on an airflow in midstream of transporting the hydrophilic fibers 10*a* to the accumulating depression 41 in a dispersed and airborne state on the airflow. Thus, the sheet fragments 10*bh* are mixed with the hydrophilic fibers 10*a* while the sheet fragments 10*bh* and the hydrophilic fibers 10*a* are being transported in a dispersed and airborne state on an airflow.

Further, in the transporting step, the absorbent particles 10*c* are supplied by using the absorbent particle dispersing tube 36, and the sheet fragments 10*bh* and the absorbent particles 10*c* are mixed while the sheet fragments 10*bh* formed in the cutting step and the absorbent particles 10*c* are being transported to the accumulating depression 41 on an airflow. In the transporting step, the position of the absorbent particle dispersing tube 36 is located more upstream than the connecting position between the suction tube 59 and the duct 3. Thus, the sheet fragments 10*bh*, the hydrophilic fibers 10*a*, and the absorbent particles 10*c* are mixed together while the absorbent particles 10*c* are being transported to the accumulating depression 41 in a dispersed and airborne state on an airflow.

Next, an accumulating step is performed for accumulating the sheet fragments 10*bh* transported in the transporting step in the accumulating depression 41, to obtain an accumulation 100*a*. In the accumulating step, not only the sheet fragments 10*bh* but also the hydrophilic fibers 10*a* and the absorbent particles 10*c* are accumulated in the accumulating depression 41 arranged in the outer circumferential surface 4*f* of the rotary drum 4 to thereby obtain an accumulation 100*a*. In the accumulating step, the sheet fragments 10*bh* and the hydrophilic fibers 10*a* are accumulated in a manner that the mixing ratio therebetween varies in the thickness direction of the accumulation 100*a*. In the present embodiment, the plurality of sheet fragments 10*bh* are supplied to inside the duct 3 from the top plate 31 side of the duct 3 at a position in midstream of the transporting direction Y of the duct 3. Thus, the sheet fragments 10*bh* are supplied from the top plate 31 side of the duct 3 in midstream of transporting the hydrophilic fibers 10*a* from the upstream side in the transporting direction Y of the duct 3. Therefore, compared to the hydrophilic fibers 10*a* that are being transported in a dispersed and airborne state on the side closer to the bottom plate 32 of the duct 3, the hydrophilic fibers 10*a* that are being transported in a dispersed and airborne state on the side closer to the top plate 31 of the duct 3 are more easily mixed with the sheet fragments 10*bh* supplied from the top plate 31 side of the duct 3. Thus, the sheet fragments 10*bh* and the hydrophilic fibers 10*a* are accumulated in a manner that the mixing ratio therebetween varies in the thickness direction of the accumulation 100*a*. In the accumulating step, the sheet fragments 10*bh* and the hydrophilic fibers 10*a* are accumulated within the accumulating depression 41 in a manner that the mixing ratio therebetween varies in the thickness direction, and the absorbent particles 10*c* are mixed and accumulated over substantially the entire region in the thickness direction.

In the accumulating step, the mixing ratio between the sheet fragments 10*bh* and the hydrophilic fibers 10*a* in the thickness direction of the accumulation 100*a* can be changed, for example, by shifting, toward the upstream side or downstream side, the position for supplying the sheet fragments 10*bh*, which include the synthetic fibers 10*b*, in midstream of the transporting direction Y of the duct 3. Alternatively, the mixing ratio between the sheet fragments 10*bh* and the hydrophilic fibers 10*a* in the thickness direction of the accumulation 100*a* can be changed, for example, by selecting whether to connect the suction tube 59 to the duct 3 on the top plate 31 side or the bottom plate 32 side. More specifically, when the position for connecting the suction tube 59, which supplies the sheet fragments 10*bh* in midstream of the transporting direction Y of the duct 3, is on the top plate 31 side and closer to the upstream side, the sheet fragments 10*bh* and the hydrophilic fibers 10*a*, which are mixed in the thickness direction of the accumulation 100*a*, are mixed more evenly.

As described above, in the accumulating depression 41 of the rotary drum 4, an accumulation 100*a* of the materials of the absorbent member is formed, wherein the sheet fragments 10*bh* and the hydrophilic fibers 10*a* are accumulated in a manner that the mixing ratio therebetween varies in the thickness direction, and the absorbent particles 10*c* are accumulated in a dispersed state in the thickness direction. In the accumulating depression 41, a two-layer structure accumulation 100*a* is likely to be formed, wherein: an accumulation layer made by accumulating the absorbent particles 10c and a fiber material constituted by only the hydrophilic fibers 10a is formed on the mesh plate 44 side of the rotary drum 4; and an accumulation layer made by accumulating the absorbent particles 10c and fiber materials formed by mixing the hydrophilic fibers 10a and the sheet fragments 10bh including the synthetic fibers 10b is superposed on the aforementioned accumulation layer. Such an accumulation 100a formed in the accumulating depression 41 is manufactured continuously over the entire circumference, in the circumferential direction (2Y direction), of the rotary drum 4. After obtaining this accumulation 100a in which the hydrophilic fibers 10a, the synthetic fibers 10b, and the absorbent particles 10c have accumulated within the accumulating depression 41, the rotary drum 4 is further rotated, and, while pressing down the accumulation 100a in the accumulating depression 41 by the press-down belt 7 which is arranged on the outer circumferential surface 4f located at the space B of the rotary drum 4, the accumulation is transported to above the vacuum conveyor 8, as illustrated in FIG. 2.

Then, as illustrated in FIGS. 2 and 3, when the accumulation 100a in the accumulating depression 41 reaches a position opposing the vacuum box 84 located at the space C of the rotary drum 4, the accumulation is released from the accumulating depression 41 by suction from the vacuum box 84, and is transferred onto the core-wrap sheet 100b introduced on the vacuum conveyor 8. The accumulation 100a, which extends continuously along the transporting direction Y, is transferred onto the central section, in the width direction X, of the core-wrap sheet 100b being transported.

Next, as illustrated in FIG. 2, one lateral side of the core-wrap sheet 100b, of the two lateral sides which extend along the transporting direction Y, is folded inward in the width direction X onto the accumulation 100a by a folding guide plate (not illustrated). Then, the other lateral side is folded inward in the width direction X onto the accumulation 100a by a folding guide plate, to thereby manufacture a continuous absorbent member 100 in which the accumulation 100a is covered by the core-wrap sheet 100b.

Then, the continuous absorbent member 100 is cut at predetermined intervals in the transporting direction Y with a cutting device (not illustrated), to thereby manufacture separate absorbent members 100. In each absorbent member 100 manufactured as above, the accumulation 100a covered by the core-wrap sheet 100b has a two-layer structure as illustrated in FIG. 1, wherein: one side (the lower side) in the thickness direction (Z direction) is the accumulation layer made of the absorbent particles 10c and a fiber material constituted by only the hydrophilic fibers 10a; and the other side (the upper side) in the thickness direction (Z direction) is the accumulation layer made of the absorbent particles 10c and fiber materials formed by mixing the hydrophilic fibers 10a and the sheet fragments 10bh including the synthetic fibers 10b. As described above, in this two-layer structure accumulation 100a, the blending ratio between the hydrophilic fibers 10a and the synthetic fibers 10b is varied in the thickness direction (Z direction).

As described above, the manufacturing method using the manufacturing device 1 involves a cutting step of cutting a continuous synthetic fiber sheet 10bs at predetermined lengths in the first direction (Y direction) and the second direction (X direction), and thereby forming sheet fragments 10bh, as illustrated in FIG. 2. Thus, sheet fragments 10bh having an intended size can be manufactured with high precision. Particularly, the plurality of cutter blades 51, 51, 51, . . . of the first cutter roller 53 are arranged at even intervals, and the plurality of cutter blades 52, 52, 52, . . . of the second cutter roller 54 are also arranged at even intervals. Thus, it is possible to easily manufacture a large amount of sheet fragments 10bh having the same size with high precision, and it is thus possible to manufacture an absorbent member 100 including an accumulation 100a in which the uniformity of the included synthetic fibers 10b is improved. By improving the uniformity of the synthetic fibers 10b included in the absorbent member 100 in this way, it is possible to suppress the occurrence of an uncomfortable feeling of contacting a foreign object during use of an absorbent article including the absorbent member 100, and also, when the absorbent member 100 absorbs body fluid, the absorbent member can absorb body fluid stably. Further, the manufacturing method using the manufacturing device 1 involves a defibrating step of defibrating a continuous hydrophilic sheet 10as and obtaining hydrophilic fibers 10a. Thus, the hydrophilic fibers 10a and the synthetic fibers 10b can be mixed through the transporting step. Further, the manufacturing method using the manufacturing device 1 can manufacture a two-layer structure accumulation 100a in which the blending ratio between the hydrophilic fibers 10a and the synthetic fibers 10b is varied in the thickness direction Z. With this manufacturing method using the manufacturing device 1, such absorbent members 100 can be manufactured efficiently and continuously.

Further, with the manufacturing method using the manufacturing device 1, as illustrated in FIG. 2, the continuous synthetic fiber sheet 10bs is cut and the sheet fragments 10bh are formed by using a first cutter roller 53 including cutter blades 51 that cut in the first direction (Y direction), and a second cutter roller 54 including cutter blades 52 that cut in the second direction (X direction). Thus, absorbent members 100 including sheet fragments 10bh with the same size can be continuously manufactured more efficiently. Particularly, in the manufacturing method using the manufacturing device 1, the sheet fragments 10bh are manufactured by using the first cutter roller 53, the second cutter roller 54, and a single receiving roller 55 arranged in opposition to the first cutter roller 53 and the second cutter roller 54. Thus, absorbent members 100 including sheet fragments 10bh with the same size can be continuously manufactured even more efficiently.

Further, with the manufacturing method using the manufacturing device 1, the supplying of the hydrophilic sheet 10as and the synthetic fiber sheet 10bs to the defibrating portion 2 and the supplying portion 5 is controlled separately by using separate feed rollers. Thus, by separately adjusting the rotation speed of the respective feed rollers, it is possible to adjust the supply amount of the hydrophilic sheet 10as to be supplied to the defibrating machine 21 via the pair of feed rollers 23, 23, or the supply amount of the synthetic fiber sheet 10bs to be supplied to the supplying portion 5 via feed rollers (not illustrated). Thus, the mixing ratio between the hydrophilic fibers 10a and the synthetic fibers 10b in the absorbent member 100 can be adjusted to a desired ratio.

Further, with the manufacturing method using the manufacturing device 1, an absorbent member 100 in which the blending ratio between the hydrophilic fibers 10a and the synthetic fibers 10b is varied in the thickness direction Z can be manufactured by using a single rotary drum 4 along with the defibrating portion 2, the duct 3, and the supplying portion 5. Thus, the scale of the facility can be made compact, and also the cost of the manufacturing device can be suppressed.

The present invention is not limited to the foregoing embodiments and can be modified as appropriate.

For example, in the cutting step, the sheet fragments 10*bh* including the synthetic fibers 10*b* are manufactured by cutting the continuous synthetic fiber sheet 10*bs* at predetermined lengths in the first direction and the second direction by using the first cutter roller 53 including the cutter blades 51 that cut in the first direction (Y direction), the second cutter roller 54 including the cutter blades 52 that cut in the second direction (X direction), and a single receiving roller 55 arranged in opposition to the first cutter roller 53 and the second cutter roller 54, as illustrated in FIG. 2. Instead, the sheet fragments 10*bh* may be manufactured by cutting the synthetic fiber sheet 10*bs* by using separate receiving rollers respectively arranged in opposition to the first cutter roller 53 and the second cutter roller 54.

Further, in the cutting step, sheet fragments 10*bh* having the same size are manufactured by cutting the synthetic fiber sheet 10*bs* by using the first cutter roller 53 having a plurality of cutter blades 51 arranged at even intervals and the second cutter roller 54 having a plurality of cutter blades 52 arranged at even intervals, as illustrated in FIG. 2. Instead, the sheet fragments 10*bh* may be manufactured by cutting the synthetic fiber sheet 10*bs* by using a first cutter roller 53 having a plurality of cutter blades 51 arranged at two or more types of intervals, or a second cutter roller 54 having a plurality of cutter blades 52 arranged at two or more types of intervals. Manufacturing in this way can form sheet fragments 10*bh* having two or more sizes, but unlike manufacturing by employing a cutter mill system, sheet fragments with intended sizes can be formed with high precision, and absorbent members having an intended absorbency can be manufactured efficiently and continuously.

Further, in the cutting step, continuous sheet fragment strips 10*bh*1 are first formed by cutting the synthetic fiber sheet 10*bs* by using the first cutter roller 53 having cutter blades 51 that cut in the first direction (Y direction), and then rectangular sheet fragments 10*bh* are manufactured by cutting the continuous sheet fragment strips 10*bh*1 by using the second cutter roller 54 having cutter blades 52 that cut in the second direction (X direction), as illustrated in FIG. 2. The order, however, can be reversed. That is, continuous sheet fragment strips 10*bh*1 extending in the second direction may first be formed by cutting the synthetic fiber sheet 10*bs* by using the second cutter roller 54 having cutter blades 52 that cut in the second direction, and then rectangular sheet fragments 10*bh* may be manufactured by cutting the continuous sheet fragment strips 10*bh*1 by using the first cutter roller 53 having cutter blades 51 that cut in the first direction.

Further, in the manufacturing device 1 illustrated in FIG. 2, the supplying portion 5 includes the first cutter roller 53 and the second cutter roller 54. Instead of these two cutter rollers, it is possible to provide a single cutter roller including, on the same circumferential surface, cutter blades 51 that cut in the first direction (Y direction) and cutter blades 52 that cut in the second direction (X direction). In cases where the supplying portion 5 includes this single cutter roller, it is preferable that the supplying portion includes a single receiving roller arranged in opposition to the single cutter roller. In a manufacturing device including the single cutter roller and the single receiving roller, it is preferable that the suction opening 581 of the suction nozzle 58 is arranged below the single cutter roller. More specifically, it is preferable that the suction opening 581 of the suction nozzle 58 is arranged more toward the downstream side, in the rotating direction of the single cutter roller, than the closest point between the single cutter roller and receiving roller. It is also preferable that the suction opening 581 of the suction nozzle 58 covers the length of an arc that is at least one-fourth of the entire outer circumference of the single cutter roller as viewed from the side surface thereof.

In cases of using this manufacturing device including the aforementioned single cutter roller and the single receiving roller, sheet fragments 10*bh* are formed by cutting the synthetic fiber sheet 10*bs* by using the single cutter roller in the cutting step. More specifically, by using the single cutter roller and the single receiving roller arranged in opposition to the cutter roller, the continuous synthetic fiber sheet 10*bs* is introduced between the cutter roller and the receiving roller and is cut in the first direction and the second direction to form the sheet fragments 10*bh*. By using a single cutter roller having, on its circumferential surface, two types of cutter blades—i.e., the cutter blades 51 that cut in the first direction and the cutter blades 52 that cut in the second direction—the scale of the facility can be made compact, and also the cost of the manufacturing device can be suppressed.

In cases of forming the sheet fragments 10*bh* by using this manufacturing device including the aforementioned single cutter roller and the single receiving roller, the plurality of sheet fragments 10*bh* remaining on the circumferential surface of the single cutter roller can be sucked efficiently in the suction step by arranging the suction opening 581 of the suction nozzle 58 below the single cutter roller and sucking the formed sheet fragments 10*bh*. The plurality of sheet fragments 10*bh* remaining on the circumferential surface of the single cutter roller can be sucked more efficiently by arranging the suction opening 581 of the suction nozzle 58 more toward the downstream side, in the single cutter roller's rotating direction, than the closest point between the single cutter roller and the receiving roller. From the same viewpoint, it is preferable that the suction opening 581 of the suction nozzle 58 covers the length of an arc that is at least one-fourth of the entire outer circumference of the single cutter roller as viewed from a side surface thereof.

Further, as illustrated in FIG. 2, in the cutting step of the present embodiment, the sheet fragments 10*bh* are manufactured by cutting the synthetic fiber sheet 10*bs* by using the first cutter roller 53 and the second cutter roller 54, but instead of using cutter rollers, the sheet fragments 10*bh* may be manufactured by cutting the synthetic fiber sheet 10*bs* by using a press machine including cutter blades 51 that cut in the first direction (Y direction) and a press machine including cutter blades 52 that cut in the second direction (X direction).

Further, in the transporting step, the hydrophilic fibers 10*a* obtained in the defibrating step and the sheet fragments 10*bh* formed in the cutting step are mixed together while the hydrophilic fibers 10*a* and the sheet fragments 10*bh* are being transported in a dispersed and airborne state by an airflow that carries the materials of the absorbent member 100 inside the duct 3 toward the rotary drum 4. The supplying portion 5 may be provided with a separation promoting portion (not illustrated) that is capable of separating the sheet fragments reliably in case the synthetic fiber sheet 10*bs* is not cut successfully in the cutting step and a plurality of the sheet fragments 10*bh* are connected. Preferably, the separation promoting portion is arranged inside the suction tube 59 or at a position in midstream of the suction tube 59. The separation promoting portion may be, for example, a device including a rod-shaped rotary shaft and a rotary blade attached helically to the rotary shaft so as to extend outward from the circumferential surface of the rotary shaft, and the device may be arranged at a position in midstream of the suction tube 59, so that, even in cases where a plurality of the sheet fragments 10*bh* passing through the suction tube 59 are connected due to cutting failure, the sheet fragments 10*bh* can be separated reliably by making the connected sheet fragments 10*bh* contact the rotating rotary blade. Alternatively, the separation promoting portion may be constructed by arranging an ejection opening of an air ejection device that ejects compressed air into the suction tube 59 to create a whirling flow, so that, even in cases where a plurality of the sheet fragments 10*bh* passing through the suction tube 59 are connected due to cutting failure, the sheet fragments 10*bh* can be separated reliably by the pressure of the compressed air and the friction with the inner wall of the suction tube 59.

Further, the present embodiment involves a defibrating step of defibrating the continuous hydrophilic sheet 10*as* by using the defibrating machine 21 and obtaining the hydrophilic fibers 10*a*, but the defibrating step does not have to be provided. Further, in the transporting step of the present embodiment, the absorbent particles 10*c* are supplied by using the absorbent particle dispersing tube 36, but the absorbent particles 10*c* do not have to be supplied.

Further, the suction step of sucking the sheet fragments 10*bh* formed in the cutting step does not have to be provided, so long as there is a transporting step of transporting the sheet fragments 10*bh* to the accumulating depression 41. Providing the suction step is, however, preferable, in terms that the sheet fragments 10*bh* can be accumulated efficiently in the accumulating depression 41 to obtain the accumulation 100*a*.

The shape of the accumulation 100*a* to be manufactured may be changed flexibly by changing the shape of the accumulating depression 41. Further, the fibers used for the synthetic fibers 10*b* may be subjected to a hydrophilizing treatment.

Further, as illustrated in FIG. 1, the absorbent member 100 includes the two-layer structure accumulation 100*a*, but the accumulation may instead be a single-layer structure accumulation 100*a* in which the sheet fragments 10*bh* including the synthetic fibers 10*b* are mixed throughout.

In relation to the foregoing embodiments, the following absorbent member manufacturing methods are further disclosed.

{1}

A method for manufacturing an absorbent member used for an absorbent article and including synthetic fibers, the method comprising:

a cutting step of cutting a continuous synthetic fiber sheet including the synthetic fibers at predetermined lengths in a first direction and a second direction intersecting with the first direction, and forming sheet fragments including the synthetic fibers;

a transporting step of transporting the formed sheet fragments to an accumulating portion; and an accumulating step of accumulating, in the accumulating portion, the sheet fragments transported in the transporting step, and obtaining an accumulation which is a constituent member of the absorbent member.

{2}

The method for manufacturing an absorbent member as set forth in clause {1}, wherein, in the cutting step, the continuous synthetic fiber sheet is cut and the sheet fragments are formed by using: a first cutter roller including cutter blades that cut in the first direction; and a second cutter roller including cutter blades that cut in the second direction.

{3}

The method for manufacturing an absorbent member as set forth in clause {2}, wherein, in the cutting step, by using the first cutter roller, the second cutter roller, and a single receiving roller arranged in opposition to the first cutter roller and the second cutter roller: the continuous synthetic fiber sheet is introduced between the first cutter roller and the receiving roller and is cut in the first direction to form continuous sheet fragment strips; and the formed continuous sheet fragment strips are transported by the receiving roller and are cut in the second direction between the second cutter roller and the receiving roller to form the sheet fragments.

{4}

The method for manufacturing an absorbent member as set forth in clause {1}, wherein, in the cutting step, the continuous synthetic fiber sheet is cut and the sheet fragments are formed by using a single cutter roller including cutter blades that cut in the first direction and cutter blades that cut in the second direction.

{5}

The method for manufacturing an absorbent member as set forth in clause {4}, wherein, in the cutting step, by using the cutter roller and a single receiving roller arranged in opposition to the cutter roller, the continuous synthetic fiber sheet is introduced between the cutter roller and the receiving roller and is cut in the first direction and the second direction to form the sheet fragments.

{6}

The method for manufacturing an absorbent member as set forth in clause {2} or {3}, wherein:

the method further comprises a suction step of sucking the sheet fragments formed in the cutting step;

in the transporting step, the sheet fragments sucked in the suction step are transported to the accumulating portion by being carried on an airflow; and in the suction step, the sheet fragments cut and formed by the second cutter roller are sucked by using a suction nozzle that sucks the sheet fragments and arranging a suction opening of the suction nozzle below the second cutter roller.

{7}

The method for manufacturing an absorbent member as set forth in clause {3}, wherein:

the method further comprises a suction step of sucking the sheet fragments formed in the cutting step;

in the transporting step, the sheet fragments sucked in the suction step are transported to the accumulating portion by being carried on an airflow; and in the suction step, a suction nozzle that sucks the sheet fragments is used, and a suction opening of the suction nozzle is arranged more toward a downstream side, in the second cutter roller's rotating direction, than a closest point between the second cutter roller and the receiving roller.

{8}

The method for manufacturing an absorbent member as set forth in clause {6} or {7}, wherein the suction opening of the suction nozzle covers a length of an arc that is at least one-fourth of an entire outer circumference of the second cutter roller as viewed from a side surface thereof.

{9}

The method for manufacturing an absorbent member as set forth in clause {4} or {5}, wherein:

the method further comprises a suction step of sucking the sheet fragments formed in the cutting step;

in the transporting step, the sheet fragments sucked in the suction step are transported to the accumulating portion by being carried on an airflow; and in the suction step, the sheet fragments cut and formed by the cutter roller are sucked by using a suction nozzle that sucks the sheet fragments and arranging a suction opening of the suction nozzle below the cutter roller.

{10}

The method for manufacturing an absorbent member as set forth in clause {5}, wherein:

the method further comprises a suction step of sucking the sheet fragments formed in the cutting step;

in the transporting step, the sheet fragments sucked in the suction step are transported to the accumulating portion by being carried on an airflow; and in the suction step, a suction nozzle that sucks the sheet fragments is used, and a suction opening of the suction nozzle is arranged more toward a downstream side, in the cutter roller's rotating direction, than a closest point between the cutter roller and the receiving roller.

{11}

The method for manufacturing an absorbent member as set forth in clause {9} or {10}, wherein the suction opening of the suction nozzle preferably covers a length of an arc that is at least one-fourth, more preferably covers a length of an arc that is at least half, of an entire outer circumference of the cutter roller as viewed from a side surface thereof.

{12}

The method for manufacturing an absorbent member as set forth in any one of clauses {1} to {11}, wherein:

the method further comprises a defibrating step of defibrating a continuous hydrophilic sheet and obtaining hydrophilic fibers; and in the transporting step, the sheet fragments are mixed with the hydrophilic fibers while the sheet fragments formed in the cutting step and the hydrophilic fibers obtained in the defibrating step are being transported to the accumulating portion.

{13}

The method for manufacturing an absorbent member as set forth in clause {12}, wherein, in the accumulating step, the sheet fragments and the hydrophilic fibers are accumulated in a manner that a mixing ratio therebetween varies in a thickness direction of the accumulation.

{14}

The method for manufacturing an absorbent member as set forth in any one of clauses {1} to {13}, wherein, in the transporting step, absorbent particles are supplied, and the sheet fragments and the absorbent particles are mixed while the sheet fragments formed in the cutting step and the absorbent particles are being transported to the accumulating portion.

{15}

The method for manufacturing an absorbent member as set forth in any one of clauses {1} to {14}, wherein the first direction is a direction in which the continuous synthetic fiber sheet is transported in the cutting step, and the second direction is a direction orthogonal to the first direction.

{16}

The method for manufacturing an absorbent member as set forth in any one of clauses {1} to {15}, wherein an average length of the sheet fragments formed in the cutting step is preferably from 0.3 to 30 mm, more preferably from 1 to 15 mm, even more preferably from 2 to 10 mm.

{17}

The method for manufacturing an absorbent member as set forth in any one of clauses {1} to {16}, wherein an average width of the sheet fragments formed in the cutting step is preferably from 0.1 to 10 mm, more preferably from 0.3 to 6 mm, even more preferably from 0.5 to 5 mm.

{18}

The method for manufacturing an absorbent member as set forth in any one of clauses {1} to {17}, wherein the accumulating portion is an accumulating depression provided in an outer circumferential surface of a rotary drum.

{19}

A device for manufacturing an absorbent member used for an absorbent article and including synthetic fibers, the manufacturing device comprising:

a duct that transports a material of the absorbent member;

an accumulating portion that is arranged on a downstream side in a transporting direction within the duct and in which the material of the absorbent member is accumulated; and a supplying portion that supplies the synthetic fibers to inside the duct, wherein:

the supplying portion includes cutter blades that cut a continuous synthetic fiber sheet including the synthetic fibers at predetermined lengths in a first direction and a second direction intersecting with the first direction, and form sheet fragments including the synthetic fibers.

{20}

The device for manufacturing an absorbent member as set forth in clause {19}, wherein the supplying portion includes: a first cutter roller including a plurality of cutter blades that cut in the first direction; and a second cutter roller including a plurality of cutter blades that cut in the second direction.

{21}

The device for manufacturing an absorbent member as set forth in clause {20}, wherein the supplying portion includes a single receiving roller arranged in opposition to the first cutter roller and the second cutter roller.

{22}

The device for manufacturing an absorbent member as set forth in clause {20} or {21}, wherein:

the supplying portion includes a suction nozzle that sucks the sheet fragments formed by using the cutter blades; and a suction opening of the suction nozzle is arranged below the second cutter roller.

{23}

The device for manufacturing an absorbent member as set forth in clause {21}, wherein:

the supplying portion includes a suction nozzle that sucks the sheet fragments formed by using the cutter blades; and a suction opening of the suction nozzle is arranged more toward a downstream side, in the second cutter roller's rotating direction, than a closest point between the second cutter roller and the receiving roller.

{24}

The device for manufacturing an absorbent member as set forth in clause {22} or {23}, wherein the suction opening of the suction nozzle covers a length of an arc that is at least one-fourth of an entire outer circumference of the second cutter roller as viewed from a side surface thereof.

{25}

The device for manufacturing an absorbent member as set forth in clause {19}, wherein the supplying portion includes a cutter roller including a plurality of cutter blades that cut in the first direction and a plurality of cutter blades that cut in the second direction.

{26}

The device for manufacturing an absorbent member as set forth in clause {25}, wherein the supplying portion includes a single receiving roller arranged in opposition to the cutter roller.

{27}

The device for manufacturing an absorbent member as set forth in clause {25} or {26}, wherein:

the supplying portion includes a suction nozzle that sucks the sheet fragments formed by using the cutter blades; and a suction opening of the suction nozzle is arranged below the cutter roller.

{28}
The device for manufacturing an absorbent member as set forth in clause {26}, wherein:
the supplying portion includes a suction nozzle that sucks the sheet fragments formed by using the cutter blades; and
a suction opening of the suction nozzle is arranged more toward a downstream side, in the cutter roller's rotating direction, than a closest point between the cutter roller and the receiving roller.

{29}
The device for manufacturing an absorbent member as set forth in clause {27} or {28}, wherein the suction opening of the suction nozzle covers a length of an arc that is at least one-fourth of an entire outer circumference of the cutter roller as viewed from a side surface thereof.

{30}
The device for manufacturing an absorbent member as set forth in any one of clauses {19} to {29}, wherein the supplying portion includes a separation promoting portion that, in cases where a plurality of the formed sheet fragments are connected, separates the plurality of sheet fragments.

{31}
The device for manufacturing an absorbent member as set forth in any one of clauses {19} to {30}, wherein the first direction is a direction in which the continuous synthetic fiber sheet is transported in the supplying portion, and the second direction is a direction orthogonal to the first direction.

{32}
The device for manufacturing an absorbent member as set forth in any one of clauses {19} to {31}, wherein an average length of the sheet fragments formed by using the cutter blades is preferably from 0.3 to 30 mm, more preferably from 1 to 15 mm, even more preferably from 2 to 10 mm.

{33}
The device for manufacturing an absorbent member as set forth in any one of clauses {19} to {32}, wherein an average width of the sheet fragments formed by using the cutter blades is preferably from 0.1 to 10 mm, more preferably from 0.3 to 6 mm, even more preferably from 0.5 to 5 mm.

{34}
The device for manufacturing an absorbent member as set forth in any one of clauses {19} to {33}, further comprising a defibrating portion that defibrates a hydrophilic sheet formed from hydrophilic fibers.

{35}
The device for manufacturing an absorbent member as set forth in any one of clauses {19} to {34}, further comprising an absorbent particle dispersing tube that supplies absorbent particles into the duct.

{36}
The device for manufacturing an absorbent member as set forth in any one of clauses {19} to {35}, further comprising:
a defibrating portion that defibrates a hydrophilic sheet formed from hydrophilic fibers; and
an absorbent particle dispersing tube that supplies absorbent particles into the duct, wherein
the absorbent particle dispersing tube is arranged between the defibrating portion and the supplying portion.

{37}
The device for manufacturing an absorbent member as set forth in any one of clauses {19} to {36}, wherein the accumulating portion is an accumulating depression provided in an outer circumferential surface of a rotary drum.

INDUSTRIAL APPLICABILITY

According to the method and device for manufacturing absorbent members of the present invention, it is possible to form, with high precision, sheet fragments having an intended size, and to efficiently and continuously manufacture absorbent members having an intended absorbency.

The invention claimed is:
1. A method for manufacturing an absorbent member for an absorbent article and including synthetic fibers, the method comprising:
a cutting step of cutting a continuous synthetic fiber sheet including the synthetic fibers at predetermined lengths in a first direction and a second direction intersecting with the first direction, and forming sheet fragments including the synthetic fibers;
a transporting step of transporting the formed sheet fragments to an accumulating portion; and
an accumulating step of accumulating, in the accumulating portion, the sheet fragments transported in the transporting step, and obtaining an accumulation which is a constituent member of the absorbent member,
wherein, in the cutting step, the continuous synthetic fiber sheet is cut and the sheet fragments are formed by using a first cutter roller including cutter blades that cut in the first direction, and a second cutter roller including cutter blades that cut in the second direction, and
wherein, in the cutting step, by using the first cutter roller, the second cutter roller, and a single receiving roller arranged in opposition to the first cutter roller and the second cutter roller:
the continuous synthetic fiber sheet is introduced between the first cutter roller and the receiving roller and is cut in the first direction to form continuous sheet fragment strips; and
the formed continuous sheet fragment strips are transported by the receiving roller and are cut in the second direction between the second cutter roller and the receiving roller to form the sheet fragments.

2. The method for manufacturing an absorbent member according to claim 1, wherein:
the method further comprises a suction step of sucking the sheet fragments formed in the cutting step;
in the transporting step, the sheet fragments sucked in the suction step are transported to the accumulating portion by being carried on an airflow; and
in the suction step, the sheet fragments cut and formed by the second cutter roller are sucked by using a suction nozzle that sucks the sheet fragments and arranging a suction opening of the suction nozzle below the second cutter roller.

3. The method for manufacturing an absorbent member according to claim 1, wherein:
the method further comprises a suction step of sucking the sheet fragments formed in the cutting step;
in the transporting step, the sheet fragments sucked in the suction step are transported to the accumulating portion by being carried on an airflow; and
in the suction step, a suction nozzle that sucks the sheet fragments is used, and a suction opening of the suction nozzle is arranged more toward a downstream side, in the second cutter roller's rotating direction, than a closest point between the second cutter roller and the receiving roller.

4. The method for manufacturing an absorbent member according to claim 1, wherein:
the method further comprises a defibrating step of defibrating a continuous hydrophilic sheet and obtaining hydrophilic fibers; and
in the transporting step, the sheet fragments are mixed with the hydrophilic fibers while the sheet fragments formed in the cutting step and the hydrophilic fibers obtained in the defibrating step are being transported to the accumulating portion.

5. The method for manufacturing an absorbent member according to claim 4, wherein, in the accumulating step, the sheet fragments and the hydrophilic fibers are accumulated in a manner that a mixing ratio therebetween varies in a thickness direction of the accumulation.

6. The method for manufacturing an absorbent member according to claim 1, wherein, in the transporting step, absorbent particles are supplied, and the sheet fragments and the absorbent particles are mixed while the sheet fragments formed in the cutting step and the absorbent particles are being transported to the accumulating portion.

7. The method for manufacturing an absorbent member according to claim 1, wherein, in the transporting step, the sheet fragments are transported by being carried on an airflow.

8. The method for manufacturing an absorbent member for an absorbent article and including synthetic fibers, the method comprising:
a cutting step of cutting a continuous synthetic fiber sheet including the synthetic fibers at predetermined lengths in a first direction and a second direction intersecting with the first direction, and forming sheet fragments including the synthetic fibers;
a transporting step of transporting the formed sheet fragments to an accumulating portion; and
an accumulating step of accumulating, in the accumulating portion, the sheet fragments transported in the transporting step, and obtaining an accumulation which is a constituent member of the absorbent member,
wherein, in the cutting step, the continuous synthetic fiber sheet is cut and the sheet fragments are formed by using a single cutter roller including cutter blades that cut in the first direction and cutter blades that cut in the second direction.

9. The method for manufacturing an absorbent member according to claim 8, wherein:
the method further comprises a suction step of sucking the sheet fragments formed in the cutting step;
in the transporting step, the sheet fragments sucked in the suction step are transported to the accumulating portion by being carried on an airflow; and
in the suction step, the sheet fragments cut and formed by the cutter roller are sucked by using a suction nozzle that sucks the sheet fragments and arranging a suction opening of the suction nozzle below the cutter roller.

10. A device for manufacturing an absorbent member for an absorbent article and including synthetic fibers, the manufacturing device comprising:
a duct that transports a material of the absorbent member;
an accumulating portion that is arranged on a downstream side in a transporting direction within the duct and in which the material of the absorbent member is accumulated; and
a supplying portion that supplies the synthetic fibers to inside the duct, wherein:
the supplying portion includes cutter blades that cut a continuous synthetic fiber sheet including the synthetic fibers at predetermined lengths in a first direction and a second direction intersecting with the first direction, and form sheet fragments including the synthetic fibers, and
wherein the supplying portion includes a separation promoting portion that, in cases where a plurality of the formed sheet fragments are connected, separates the plurality of sheet fragments.

11. The device for manufacturing an absorbent member according to claim 10, wherein the supplying portion includes
a first cutter roller including a plurality of cutter blades that cut in the first direction, and
a second cutter roller including a plurality of cutter blades that cut in the second direction.

12. The device for manufacturing an absorbent member according to claim 11, wherein the supplying portion includes a single receiving roller arranged in opposition to the first cutter roller and the second cutter roller.

13. The device for manufacturing an absorbent member according to claim 12, wherein:
the supplying portion includes a suction nozzle that sucks the sheet fragments formed by using the cutter blades; and
a suction opening of the suction nozzle is arranged more toward a downstream side, in the second cutter roller's rotating direction, than a closest point between the second cutter roller and the receiving roller.

14. The device for manufacturing an absorbent member according to claim 11, wherein:
the supplying portion includes a suction nozzle that sucks the sheet fragments formed by using the cutter blades; and
a suction opening of the suction nozzle is arranged below the second cutter roller.

15. The device for manufacturing an absorbent member according to claim 10, wherein the supplying portion includes a cutter roller including a plurality of cutter blades that cut in the first direction and a plurality of cutter blades that cut in the second direction.

16. The device for manufacturing an absorbent member according to claim 15, wherein:
the supplying portion includes a suction nozzle that sucks the sheet fragments formed by using the cutter blades; and
a suction opening of the suction nozzle is arranged below the cutter roller.

17. The device for manufacturing an absorbent member according to claim 10, further comprising:
a defibrating portion that defibrates a hydrophilic sheet formed from hydrophilic fibers; and
an absorbent particle dispersing tube that supplies absorbent particles into the duct, wherein
the absorbent particle dispersing tube is arranged between the defibrating portion and the supplying portion.

* * * * *